Oct. 4, 1938. T. E. GRAHAM Plant Pat. 293
APPLE TREE
Original Filed Dec. 5, 1936
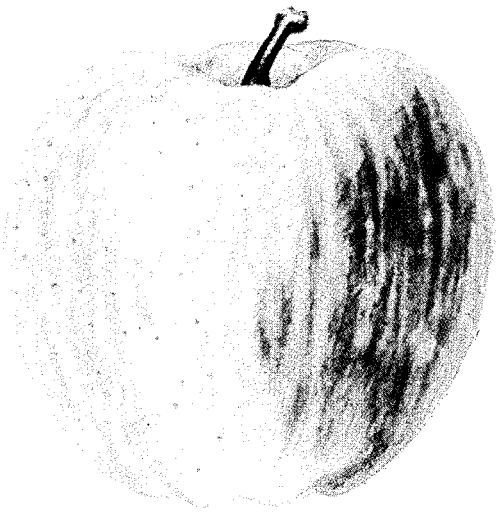
INVENTOR
Thomas Elwood Graham
By Orville M. Kile
PLANT PATENT AGENT Patented Oct. 4, 1938

Plant Pat. 293

UNITED STATES PATENT OFFICE

293

APPLE TREE

Thomas Elwood Graham, Kent County, Mich., assignor to Greening Nursery Company, Monroe, Mich., a corporation of Michigan Original application December 5, 1936, Serial No. 114,505. Divided and this application November 5, 1937, Serial No. 173,017

1 Claim. (Cl. 47—62)

My present discovery is a mutation of the Northern Spy type of apple and relates particularly to striped fruit of increased size and earlier ripening date than fruit of the Northern Spy, also to earlier bearing age of the trees.

This application is a division of application No. 114,505, filed on December 5, 1936, now Plant Patent 278.

The variety originated as a sport in an orchard in northern Michigan made up mostly of Northern Spy trees but including Wagener, Jonathan, Wealthy, Grimes Golden, and McIntosh trees. This particular variety is a sport from a tree which produced other sports identical in most respects but varying in color. Grafts topworked on other trees have for several seasons reproduced apples true to this type.

The tree and the growth habits of this new variety are essentially the same as those of the Northern Spy and can be described by any standard description of the Northern Spy. Such a description from the 1905 edition of "The Apples of New York" is quoted in part as follows:

"Tree—Large, vigorous; branches long, moderately stout, curved. Form upright, dense, becoming roundish with willowy slender laterals somewhat inclined to droop. Twigs long to medium in length, erect, straight or somewhat crooked, slender to moderately stout; internodes long to rather short. Bark dull, dark brownish-red mingled with olive-green lightly streaked with thick scarf-skin; heavily pubescent. Lenticels numerous, conspicuous, small, roundish or oblong, slightly raised. Buds deeply set in bark medium to small, broad, plump, obtuse, appressed, slightly pubescent."

The accompanying illustration shows a specimen of this new variety.

Following is a more detailed description of the fruit of this variety.

*Size.*—Large to very large, many attaining a transverse diameter of 3½ to 4 inches.

*Weight.*—8 to 12 ounces.

*Form.*—Slightly irregular, nearly symmetrical, some specimens oblate, others longer.

*Cavity.*—Large; ¾ inch deep and 1 inch wide; even; flaring; covered with russet which radiates upward.

*Basin.*—Almost same depth and shape as cavity, but somewhat shallower and narrower.

*Stem.*—Medium to long; brownish green, medium thickness.

*Skin.*—Thin, smooth, glossy.

*Color.*—Striped, consisting of various shades of red ranging from Scarlet to Oxblood Red (Pl. I of Ridgway's Color Standards and Nomenclature), over a yellow background. Minute yellowish dots are spread over the entire surface.

*Flesh:*—

*Color.*—Creamy white.

*Texture.*—Firm, juicy, fine, tender, crisp, excellent quality.

*Flavor.*—Mild but sprightly; subacid; very agreeable; not as sour as Northern Spy nor as sweet as Delicious.

*Aroma.*—Pleasing and distinct.

*Core.*—Median position; small.

*Bundle area (longitudinal).*—Medium; slightly unsymmetrical.

*Seeds.*—Medium size; dark brown; pointed; numerous.

*Eating quality.*—Good.

*Storing and keeping qualities.*—Excellent.

*Maturity.*—Ripens earlier than Northern Spy, about same time as McIntosh.

What I claim is:

A new and distinct variety of apple tree essentially as shown and described, characterized particularly by its earlier bearing age, and the larger size, earlier ripening and more agreeable flavor of the fruit as compared with Northern Spy; also by the striped red-over-yellow-background color of its fruit as described and shown.

THOMAS ELWOOD GRAHAM.